United States Patent [19]
Paget et al.

[11] 4,046,770
[45] Sept. 6, 1977

[54] N-(6-ACYLOXYBENZOTHIAZOL-2-YL)-N'-PHENYL (OR SUBSTITUTED PHENYL)UREAS

[75] Inventors: Charles J. Paget, Indianapolis; James H. Wikel, Greenwood, both of Ind.

[73] Assignee: Eli Lilly and Company, Indianapolis, Ind.

[21] Appl. No.: 635,832

[22] Filed: Nov. 28, 1975

Related U.S. Application Data

[63] Continuation-in-part of Ser. No. 502,129, Aug. 30, 1974, Pat. No. 3,932,434.

[51] Int. Cl.$^2$ .......................................... C07D 277/82

[52] U.S. Cl. ..................................... 260/305; 424/270
[58] Field of Search ........................................ 260/305

[56] References Cited

FOREIGN PATENT DOCUMENTS 1,296,561  11/1972  United Kingdom

*Primary Examiner*—Donald G. Daus
*Assistant Examiner*—Mark L. Berch
*Attorney, Agent, or Firm*—James L. Rowe; Everet F. Smith

[57] ABSTRACT

N-(6-Acyloxybenzimidazol-2-yl)-N'-phenyl (or substituted pehnyl)ureas are useful as immune regulants.

9 Claims, No Drawings

N-(6-ACYLOXYBENZOTHIAZOL-2-YL)-N'-PHENYL (OR SUBSTITUTED PHENYL)UREAS

CROSS REFERENCE TO RELATED APPLICATION

This is a continuation-in-part, of Serial No. 502,129 filed Aug. 30, 1974. U.S. Pat. No. 3,932,434 issued Jan. 13, 1976.

BACKGROUND OF THE INVENTION

2-Substituted benzimidazoles, benzothiazoles and benzoxazoles have recently been proposed for a variety of uses, mainly in the agricultural field. For example, 2-trifluoromethylbenzimidazoles are reported to be extremely active herbicides according to Great Britain Pat. No. 1,087,561. The compounds therein disclosed are also reported to have molluscicidal, insecticidal and fungicidal properties. Other 2-substituted benzimidazoles have been found to be active coccidiostats. In particular, 2-(4-thiazolyl) benzimidazole (thiabendazole) is presently being marketed as an anthelmintic. In addition, certain 2-hydroxybenzylbenzimidazoles have been revealed as having anti-viral properties (see U.S. Pat. No. 3,331,739). While the use of benzoxazoles and and benzothiazoles in the above areas has not been quite as thoroughly explored as that of benzimidazoles, there is, nevertheless, considerable interest in compounds of this structure, particularly as coccidiostats.

Urea derivatives of the above classes of compounds are sparingly described in the art. N-(benzothiazol-2-yl)-N'-phenyl urea is described in *Chem. Abs.*, 29, 2660; 55, 8389; 57, 801; the corresponding 4-methyl compound is described in *Chem. Abs.*, 25, 104; 50, 1776–1777 and the corresponding 5-methoxy derivative is described in *Chem. Abs.*, 52, 20673. N-(Benzimidazol-2-yl)-N'-phenyl urea is described in *Beilstein*, 24 (II), 62 and in *Chem. Abs.*, 15, 3077. In addition, U.S. Pat. No. 3,299,085 discloses N-(benzothiazol-2-yl) or N-(benzoxazol-2-yl)-N'-$C_1$-$C_5$ aliphatic ureas as intermediates in the preparation of certain herbicides, and U.S. Pat. No. 3,162,644 describes benzoxazol-2-yl ureas, useful as plant growth regulators and muscule relaxants. U.S. Pat. Nos. 3,399,212; 3,336,191; and 3,401,171 disclose benzimidazolyl ureas said to be anthelmintics. Finally, South African Pat. No. 68/4748 (Derwent Pharmdoc basic number 36565) discloses benzothiazolyl ureas as antiseptics in detergent compositions.

Recently, immune suppressant and immune regulant agents have come into prominence because of their use during transplants of organs from one human to another such as heart transplants, and in particular, kidney transplants. It is part of the defense methanism of humans to attempt to remove foreign antigens (in this case, the transplanted organ) by the immune reaction. Thus, in all of the organ transplant operations, it has been necessary to give large doses of an immune suppressant prior to the operation and continuing thereafter in order to prevent the host from rejecting the donor organ. The immune suppressant of choice is azathioprine, IMURAN® (U.S. Pat. No. 3,056,785).

Belgian Pat. No. 744,970 granted July 27, 1970 (see also United Kingdom Pat. No. 1,296,561 published Nov. 15, 1972) describes the use of a number of 6-substituted-benzothiazolyl phenyl ureas including N-(6-methoxybenzothiazol-2-yl)-N'-phenyl urea. The compounds are said to be useful as immune suppressants and immune regulants.

The immune response is composed of a sequence of cellular transformations and biochemical events leading to a bimodal response to foreign substances (antigens). Cells which are to participate in the response evolve from stem cells which originate in the bone marrow and are seeded out to the peripheral lymphoid organs. From these latter sites, following antigenic stimulus, the body's response is mounted in the form of plasma cells (which produce antibody) and specific immune lymphocytes. Antibody is released into the circulatory system and thus may act at a distance from the producing cell (humoral immunity). Specific immune lymphocytes also enter the circulatory system and act at the site of injury (cellular immunity). The reaction of antibody with antigen triggers the release of histamine from basophilic leucocytes; histamine, in turn, alters the permeability of blood vessels, speeding the influx of both antibody and specific immune lymphocytes into the sites of injury. Thus, the immune response is composed of a series of biochemical evants in a sequence of cells at various sites in the body. It can be altered—suppressed, in the case of the compounds herein discussed—at a number of biochemical or cellular developmental sites.

Antihistamines only affect a secondary reaction in the immune response, having no direct effect on antibody-producing cells or specific immune lymphocytes. A number of agents, currently in use as immuno-suppressive drugs, act further back in the chain of events called herein the immune response. Certain antiinflammatory steroids, e.g., cortisone, suppress production of antibody and specific immune lymphocytes, but also radically deplete normal lymphoid tissue and have other undesirable side effects. Several antineoplastic drugs, e.g., azathioprine, cyclophosphamide, and methotrexate, are employed as immunosuppressives, but they also deplete normal lymphoid tissue and radically depress other bone-marrow-derived cells. The general cytotoxicity of the latter drugs is to be expected in view of their having been selected on the basis of toxicity against a spectrum of cell types.

It is an object of this convention to provide a method of altering the immune response through the use of agents selected on the basis of specificity of action against cells functioning in the immune response.

SUMMARY OF THE INVENTION

This invention provides N-(6-acyloxybenzothiazol-2-yl)-N'-phenyl ureas represented by Formula I

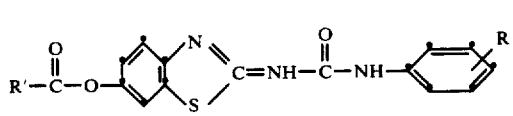

wherein R is hydrogen, halo, ($C_1$-$C_3$) alkyl or ($C_1$-$C_3$) alkoxy and R' is ($C_1$-$C_3$) alkyl or phenyl. In the above formula the term ($C_1$-$C_3$) alkyl includes methyl, ethyl, n-propyl and isopropyl. Thus, the term ($C_1$-$C_3$) alkoxy includes methoxy, ethoxy, n-propoxy and isopropoxy. The term "halo" includes fluoro, chloro, bromo and iodo.

Compounds illustrative of the scope of the above formula include:

N-(6-acetoxybenzothiazol-2-yl)-N'-(3-methoxyphenyl)urea,

N-(6-propionyloxybenzothiazol-2-yl)-N'-(2-ethyl-phenyl)urea,

N-(6-isopropionyloxybenzothiazol-2-yl)-N'-(4-n-propoxyphenyl)urea,

N-(6-butyryloxybenzothiazol-2-yl)-N'-(2-chlorophenyl)urea,

N-(6isobutyryloxybenzothiazol-2-yl)-N'-(4-bromophenyl)-urea,

N-(6-benzoyloxybenzothiazol-2-yl)-N'-(3-fluorophenyl)urea,

N-(6-acetoxybenzothiazol-2-yl)-N'-(4-iodophenyl)urea,

N-(6-propionyloxybenzothiazol-2-yl)-N'-(2-ethoxyphenyl)urea,

N-(6-isopropionyloxybenzothiazol-2-yl)-N'-(4-isopropoxyphenyl)urea,

N-(6-butyryloxybenzothiazol-2-yl)-N'-(4-isopropylphenyl)-urea,

N-(6-isobutyryloxybenzothiazol-2-yl)-N'-(3-tolyl)urea,

N-(6-benzoyloxybenzothiazol-2-yl)-N'-(4-tolyl)urea, and the like compounds.

The compounds represented by Formula I are high-melting, white, crystalline solids, which can be prepared by acylating the hydroxyl group of the corresponding N-(6-hydroxybenzothiazol-2-yl)-N'-phenyl (or substituted phenyl)urea (II) with the anhydride of acetic, propionic, isopropionic, butyric, isobutyric or benzoic acid in the presence of pyridine as illustrated below:

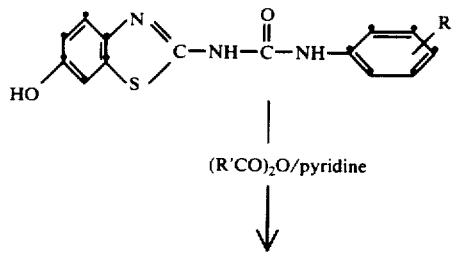

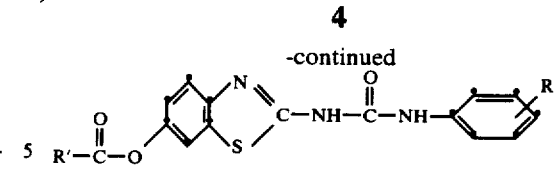

It will be recognized by those skilled in the art that the compounds of Formula I wherein R' is phenyl can have the phenyl ester moiety substituted by inert groups such as $(C_1-C_3)$ alkyl or alkoxy, halo, nitro or trifluoromethyl. Such compounds have immune regulant properties similar to those of the parent phenyl ester compounds, and are included within the scope of this invention.

The required reactants represented by Formula II can be prepared by either of the two following synthetic procedures. In both procedures, the starting material is 2-amino-6-hydroxybenzothiazole prepared by condensing quinone and thiourea according to the procedure of J. Org. Chem. 35, 4103 (1970) or by demethylating 2-amino-6-methoxybenzothiazole by the procedure of J. Hetero. Chem., 10, 769 (1973). In the first synthesis, a carbamate group is formed on the 2-amino group of the 2-amino-6-hydroxybenzothiazole with a phenyl chloroformate, for example, p-nitrophenylchloroformate. The carbamate is then reacted with trimethylsilyl chloride in accordance with the procedure of Greber and Kricheldorf, Angew. Chem. Internat. Edit., 7, 941 (1968). The trimethylsilyl group has a double function in this process. In the first place, it transforms the p-nitrophenyl carbamate group to an isocyanate group. Secondly, the trimethylsilyl group acts as a protecting group on the free hydroxyl of the benzothiazole moiety, thus preventing a reaction between the free hydroxyl and the isocyanate simultaneously formed. The 6-trimethylsilyloxybenzothiazolyl-2-isocyanate thus formed can then react readily with aniline or a suitably substituted aniline to form a urea. Addition of water to the reaction mixture serves to hydrolyze the trimethylsilyl protecting group and thus produce the required reactant having the structure of Formula II above. This synthetic process is more fully illustrated in Reaction Scheme I which follows.

Reaction Scheme I

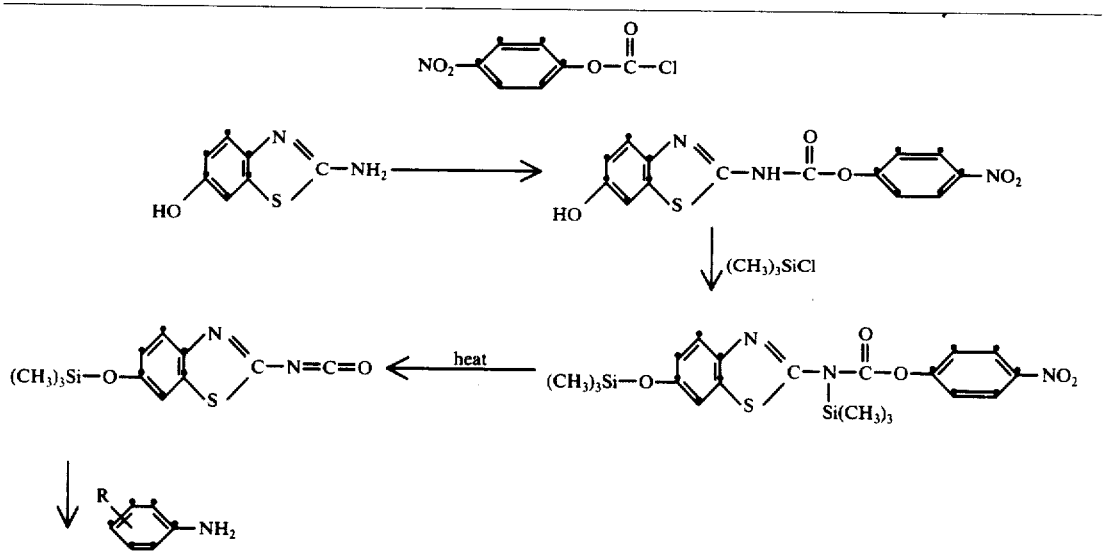

-continued
Reaction Scheme I

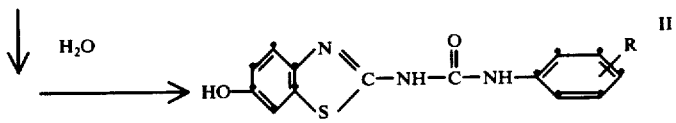

In Reaction Sequence I, the phenyl chloroformate used has been illustrated with reference to the p-nitro derivative. Other chloroformates can, of course, be used to form carbamates with the aminohydroxybenzothiazole as, for example, the unsubstituted phenylchloroformate or a tolylchloroformate. The carbamates derived from these other chloroformates, however, require somewhat higher reaction temperatures and/or longer reaction times for the decomposition of the trimethylsilyl compound to form the benzothiazolylisocyanate. In addition, in Reaction Sequence I, the silylation has been illustrated with the use of trimethylsilyl chloride. However, as pointed out by Greber and Kricheldorf (loc. cit.), either mono or bis (trimethylsilyl) acetamide can also be used to prepare the disilylated derivative.

The second synthetic procedure available for the preparation of the reactants of Formula II above involves the reaction of the 2-amino-6-hydroxybenzothiazole with a stoichiometric excess (up to two moles) of a phenylisocyanate. The isocyanate reacts predominately and preferentially with the carbamate group to form the urea moiety. However, the competing reaction to form a 6-carbamoyloxy derivative proceeds at a measurable rate. The larger the excess of isocyanate employed, the greated the yield of urea, but also the greater the amount of 6-carbamoyloxy derivative. Conversion of the 6-carbamoyloxy derivative to the desired 6-hydroxy derivative is readily accomplished, however, by preferential hydrolysis in base, as disclosed and claimed in U.S. Pat. No. 3,932,435 issued January 13, 1976.

This invention is further illustrated by the following specific examples: (All pKa's cited were determined in a 66 percent dimethylformamide/water system).

PREPARATION OF STARTING MATERIALS

EXAMPLE 1

Preparation of N-(6-Hydroxybenzothiazol-2-yl)-N'-Phenylurea

A slurry was prepared containing 16.7 g. of 2-amino-6-hydroxybenzothiazole hydrochloride, prepared by the method of *J. Org. Chem.*, 35, 4103 (1970), in 300 ml. of acetone and 11 g. of potassium bicarbonate. The slurry was stirred under anhydrous conditions while 22.4 g. of p-nitrophenylchloroformate in 300 ml. of acetone were added thereto in dropwise fashion. The reaction mixture was stirred for about 18 hours and then poured into three liters of water. The reaction mixture was filtered, and the filter cake, comprising p-nitrobenzyl-6-hydroxybenzothiazole-2-carbamate formed in the above reaction, was washed with ether. The compound crystallized as the hemihydrate.

Analysis calculated for $C_{14}H_9N_3O_5S \cdot \frac{1}{2} H_2O$. Calc.: C, 51.85; H, 2.88; N, 13.33; Found: C, 51.74; H, 3.40; N, 12.74.

A slurry was prepared containing 600 mg. of the above carbamate in 25 ml. of acetone. About 0.5 ml. of aniline was added in dropwise fashion. The reaction mixture was stirred at ambient temperature while 0.3 ml. of trimethylsilyl chloride were added in dropwise fashion via a syringe. The resulting mixture was refluxed for about 18 hours yielding a yellow solution. The reaction mixture was cooled, poured into water with stirring. The reaction mixture was cooled, poured into water with stirring, and then filtered. The filter cake was washed with ether and dried. The filter cake comprised N-(6-hydroxybenzothiazol-2-yl)-N'-phenylurea formed in the above reaction. m.p. above 250° C. Yield = 60 percent. Characteristic Mass spectral fragments at 285,212, 192, and 166; pKa = 10.9.

Analysis calculated for $C_{14}H_{11}N_3O_2S$. Calc.: C, 58.93; H, 3.89; N, 14.73; Found: C, 58.34; H, 3.76; N, 13.76.

The following compounds were prepared by the above procedure: N-(6-hydroxybenzothiazol-2-yl)-N'-(4-methoxyphenyl)urea; pKa = 11.1; Characteristic mass spectral fragments at 315, 192, and 166. m.p. above 250° C.

Analysis calculated for $C_{15}H_{13}N_3O_3S \cdot \frac{3}{4} H_2O$. Calc.: C, 57.13; H, 4.16; N, 13.33; Found: C, 56.90; H, 4.40; N, 13.37.

N-(6-hydroxybenzothiazol-2-yl)-N'-(2-fluorophenyl)-urea. Melting point above 250° C. One spot material by thin layer chromatography. pKa = 10.3; Characteristic mass spectral fragments at 303, 192, and 166.

Analysis calculated for $C_{14}H_{10}FN_3O_2S$. Calc.: C, 55.44; H, 3.32; N, 13.85; Found: C, 55.28; H, 3.47; N, 13.31.

N-(6-hydroxybenzothiazol-2-yl)-N'-(2-tolyl)urea. Melting point above 250° C. One spot material by thin layer chromatography; pKa = 10.6

Analysis calculated for $C_{15}H_{13}N_3O_2S \cdot \frac{3}{4} H_2O$. Calc.: C, 57.88; H, 4.82; N, 13.50; Found: C, 57.42; H, 4.27; N, 13.18.

EXAMPLE 2

Alternate Preparation of N-(6-hydroxybenzothiazol-2-yl)-N'-phenylurea

A slurry of 152 g. of 2-amino-6-hydroxybenzothiazole was prepared in 3 liters of acetone. A solution of 109 g. of phenylisocyanate and 150 ml. of acetone was added thereto in dropwise fashion. After the addition had been completed, the reaction mixture was heated at refluxing temperature overnight. The reaction mixture was cooled to about 50° C. and decolorizing charcoal added. The mixture was filtered, and a second batch of 109 g. of phenylisocyanate in acetone added to the filtrate. The reaction mixture was again heated to refluxing temperature for about 2 hours. The reaction mixture was cooled, and a white solid comprising N-(6-phenylcarbamoyloxybenzothiazol-2-yl)-N'-phenylurea precipitated. The precipitate was separated by filtration, and the filter cake washed with acetone. Yield = 73 percent.

Analysis calculated for $C_{21}H_{16}N_4O_3S$. Calc.: C, 62.52; H, 3.75; N, 13.89; S, 7.95; Found: C, 62.30; H, 3.97; N, 13.69; S, 7.76.

Melting point above 250° C.

Four grams of the above carbamoyloxybenzothiazolyl phenyl urea were dissolved in 150 ml. of anhydrous methanol. A 10 percent slurry of 0.5 g. of sodium methylate in methanol was added with stirring. The reaction mixture was stirred at room temperature overnight. Thin layer chromatography showed about 50 percent of the carbamoyl group had been removed by hydrolysis. The reaction mixture was then slowly heated and the progress of the reaction continually checked by thin layer chromatography. After two hours of heating at about 45° C., the hydrolysis was substantially 100 percent complete. The reaction mixture was then cooled and carefully acidified to pH=about 4 with 10 percent aqueous hydrochloric acid. N-(6-hydroxybenzothiazol-2-yl)-N'-phenylurea formed in the above reaction was separated by filtration. The filter cake was washed with methanol and then ether. Examination of the NMR spectra indicated that the phenyl carbamoyl group was no longer present in the molecule; this fact was further substantiated by the UV shifts in acid and base.

PREPARATION OF FINAL PRODUCTS

EXAMPLES 3–6

Preparation of
N-(6-acyloxybenzothiazol-2-yl)-N'-phenylureas
(General Procedure)

One hundredth of a mole of the appropriate N-(6-hydroxybenzothiazol-2-yl)-N'-phenyl(or substituted phenyl)-urea is dissolved in 25 ml. of pyridine. One equivalent (0.01 mole) of acetic, propionic, butyric or isobutyric anhydride is added and the reaction mixture is stirred for 12 hours. The mixture is poured over ice. The precipitated product is filtered, washed with water and ethyl ether, and dried.

The following compounds were prepared by the method described above.

N-(6-Acetoxybenzothiazol-2-yl)-N'-phenylurea, m.p. 210°–213° C, yield 2.3 g. (70 percent).

Analysis $C_{16}H_{13}N_3O_3S$ MW 327. Calcd.: C, 58.70; H, 4.00; N, 12.84; Found: C, 58.98; H, 4.22; N, 12.86.

N-(6-Propionyloxybenzothiazol-2-yl)-N'-phenylurea, m.p. 212°–215° C., yield 2.8 g. (81.6 percent).

Analysis $C_{17}H_{15}N_3O_3S$ MW 341. Calcd.: C, 59.81; H, 4.43; N, 12.31; Found: C, 59.50; H, 4.69; N, 11.99.

N-(6-Butyryloxybenzothiazol-2-yl)-N'-phenylurea, m.p. 207°–211° C., yield 2.3 g. (65 percent).

Analysis $C_{18}H_{17}N_3O_3S$ MW 354. Calcd.: C, 60.49; H, 5.36; N, 11.76; Found: C, 60.11; H, 5.30; N, 11.39.

N-(6-Isobutyryloxybenzothiazol-2-yl)-N'-phenylurea, m.p. 212°–215° C., yield 3.4 g. (96 percent).

Analysis $C_{18}H_{17}N_3O_3S$ MW 354. Calcd.: C, 60.49; H, 5.36; N, 11.76; Found: C, 60.59; H, 5.24; N, 11.50.

EXAMPLE 7

N-(6-benzoyloxybenzothiazol-2-yl)-N'-phenylurea

Two and eight tenths grams (0.01 mole) of N-(6-hydroxybenzothiazol-2-yl)-N'-phenylurea were dissolved in 25 ml. of pyridine. Two and three-tenths grams (0.01 mole) of benzoic anhydride were added and the mixture was stirred for 12 hours. The mixture was poured over ice. The precipitated product was filtered, washed with water and ethyl ether and dried. The yield was 2.3 g. (59 percent) of N-(6-benzoyloxybenzothiazol-2-yl)-N'-phenylurea, m.p. 245°–249° C.

Analysis: $C_{21}H_{15}N_3O_3S$ MW 389. Calcd.: C, 64.77; H, 3.88; N, 10.79; Found: C, 64.36; H, 4.19; N, 10.60.

The compositions of this invention are useful in altering the immune reaction in mammals. Thus, the compounds can be classed as "immune regulating agents" by which is meant an agent which can decrease the formation of antibodies to foreign protein. This activity can thus also be characterized an anti-allergic in that the allergic reaction is part of the defense mechanism of the body (the immune mechanism) against foreign antigens. (This activity is quite different from an antihistamine activity which affects only the effects of histamine released by an antibody-antigen reaction.) Although immune regulating activity as determined in mice using sheep erythrocytes as the antigen, it should be understood that the same types of activity would be shown against any foreign protein (antigen) in any species in mammal.

The ability of compounds according to the above Formula I to alter immune mechanisms in a host animal was measured by their activity according to the following test.

Test Methods

Groups of five 20-gram, male, random-bred, Swiss mice received intravenous injections of $5 \times 10^7$ sheep red blood cells. The cells for these injections were prepared from lamb's blood (collected in Alsever's solution) by washing three times with 0.85 percent saline and resuspending in 0.85 percent saline. Ten daily doses of the compounds, suspended in saline containing 0–125 percent methocel and 0.2 percent emulphor, were administered orally in 0.1 ml doses, commencing three days prior to red blood cell injection. Several dose levels of each drug were employed, at two-fold increments. A control group of mice, receiving a red blood cell injection and ten daily doses of vehicle instead of drug, was included. Six days after the antigen injections, the mice were bled by cardiac puncture and the sera from each five-mouse group pooled. The serum pools, following complement inactivation, were assayed for hemagglutinin content by standard procedures, utilizing a mixture of serial two-fold saline dilutions of the test sera with 0.5 percent sheep red blood cell suspensions in plastic depression trays. Following incubation of the trays for 3 hours at 37° C., the hemagglutination patterns were graded. A four-fold (75 percent) or greater antibody reduction (in the test serum as compared with the control serum) was considered significant. The results were expressed as the lowest drug dose producing 75 percent or greater antibody reduction.

The compounds were tested further by a modified serum assay procedure as described hereinbelow.

Individual Serum Assay Procedure

In these tests, the procedure described above was modified by the use of 10-mouse groups, rather than five-mouse groups. The mice were bled as before, but the sera were titered individually rather than as a pool. Mean hemagglutinin values ($log_2$) ± S.E. were calculated for each 10-mouse group and p values (by Student's T Test), in comparison with the control group, were determined. The lowest drug dose significantly (p <0.01) lowering antibody titer defined the endpoint. Drugs were administered in 10 daily doses; in these instances, the mice were bled on 7th, rather than the 6th, post-antigen day. Typical results obtained in the individual serum assay test with representative compounds of the invention are summarized in Table I.

In Table I the first column gives the substituent varient R' of the compounds of Formula I wherein R is hydrogen and the second column the immunosuppressive endpoint as the lowest drug dose in milligrams per kilogram which significantly lowers the antibody titer.

Table I. Immunosuppressive Activity of N-(6-Acyloxybenzothiazol-2-yl)-N'-Phenylureas (Individual Serum Assay Procedure)

| R' (Substituent) | Endpoint Dose (mg/Kg) (p<0.01) |
|---|---|
| methyl | 12.5 |
| ethyl | 3.1 |
| propyl | 3.1 |
| isopropyl | 12.5 |
| phenyl | >12.5 |

The compounds of this invention are useful in organ transplant operations where they can be used to prevent the host from rejecting the donor organ. In addition to their use in organ transplant operations, immune regulating agents are also useful in various diseases of little-understood etiology, denominated generically as "auto-immune" diseases. These diseases include: auto-immune hemolytic anemia, idiopathic thrombocytopenic purpura, lupus erythematosus, lupoid hepatitis, lupus nephritis, glomerulonephritis, the nephrotic syndrome, Goodpasture's syndrome, Wegener's granulomatosis, scleroderma, Sezary's disease, psoriasis, uveitis, rheumatoid arthritis, ulcerative colitis, thyroiditis and mumps orchitis. Immune suppressant agents may be more or less useful in the treatment of the above diseases depending upon the degree to which the disease is dependent upon an auto-immune mechanism.

Routes of administration include oral, intraperitoneal, topical and subcutaneous routes. For oral administration, the immune regulant can be dissolved or suspended in polyethylene glycol and mixed with corn oil, at a rate of 1-200 mg./ml. A particularly useful medium for oral administration contains 50 percent polyethylene glycol 200, 40 percent corn oil and 10 percent polyoxyethylene sorbitol monostearate. Aqueous vehicles, to which may be added surface-active agents, are also useful. For topical application, the compound is preferably administered in ethanol or in the above polyethylene glycol-corn oil-surfactant composition whereas for subcutaneous injection an isotonic solution is used. The immune-regulant is present in the particular vehicle at the rate of from 1 to 200 mg./ml.

The heterocyclic ureas useful in altering the immune response according to the processes of this invention, as can be seen, differ from a majority of the known immune regulants and immunosuppressants in the mechanism of their action on the mammalian host. They do not act by directly antagonizing the action of histamine as do the anti-histamine drugs. On the other hand, they do not depress bone-marrow function as do the antineoplastic drugs frequently used in connection with tissue transplants. The heterocyclic ureas of this invention more closely resemble the corticoids in their effects on the immune response, but even here there is a fundamental difference in that the corticoids deplete lymphoid tissue and the heterocyclic ureas of this invention do not. Thus, it is apparent that these agents function through a mechanism which neither depletes normal lymphoid mass nor depresses bone marrow, thus avoiding the major drawbacks of the currently used immunosuppressive drugs—the corticosteroids and antineoplastic drugs.

We claim:

1. A compound of the formula

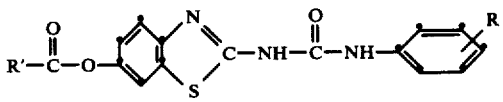

wherein R is hydrogen, halo, $(C_1-C_3)$ alkyl or $(C_1-C_3)$ alkoxy and R' is $(C_1-C_3)$ alkyl.

2. A compound of claim 1 wherein R is hydrogen and R' is $(C_1-C_3)$ alkyl.

3. The compound of claim 2 which is N-(6-acetoxybenzothiazol-2-yl)-N'-phenylurea.

4. The compound of claim 2 which is N-(6-propionyloxybenzothiazol-2-yl)-N'-phenylurea.

5. The compound of claim 2 which is N-(6-butyryloxybenzothiazol-2-yl)-N'-phenylurea.

6. A compound of the formula

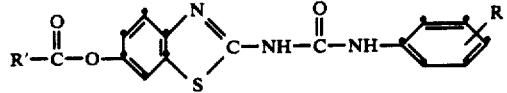

wherein R is hydrogen, halo, $(C_1-C_3)$ alkyl or $(C_1-C_3)$ alkoxy and R' is phenyl.

7. A compound of claim 6 wherein R is hydrogen and R' is phenyl.

8. The compound of claim 7 which is N-(6-benzoyloxybenzothiazol-2-yl)-N'-phenylurea.

9. The compound of claim 2 which is N-(6-isobutyryloxybenzothiazol-2-yl)-N'-phenylurea.

* * * * *